(12) United States Patent
Student et al.

(10) Patent No.: US 8,206,729 B2
(45) Date of Patent: Jun. 26, 2012

(54) COMPOSITIONS FOR TOPICAL APPLICATIONS COMPRISING BORON NITRIDE

(75) Inventors: Joerg Student, Stuttgart (DE); Rickson Sun, Palo Alto, CA (US); Kristi Scherler, Akron, OH (US); Paul Hans, Medina, OH (US); Jon Leist, North Olmsted, OH (US); Gregory W. Shaffer, Strongsville, OH (US)

(73) Assignee: Momentive Performance Materials Inc., Albany, NY (US)

( * ) Notice: Subject to any disclaimer, the term of this patent is extended or adjusted under 35 U.S.C. 154(b) by 811 days.

(21) Appl. No.: 11/554,705

(22) Filed: Oct. 31, 2006

(65) Prior Publication Data

US 2007/0207102 A1 Sep. 6, 2007

Related U.S. Application Data

(60) Provisional application No. 60/778,539, filed on Mar. 2, 2006, provisional application No. 60/807,534, filed on Jul. 17, 2006.

(51) Int. Cl.
*A61K 8/02* (2006.01)
*A61K 33/22* (2006.01)
*A01N 59/14* (2006.01)

(52) U.S. Cl. ........................ 424/401; 424/657

(58) Field of Classification Search .................... None
See application file for complete search history.

(56) References Cited

U.S. PATENT DOCUMENTS

| | | | |
|---|---|---|---|
| 3,250,680 A | 5/1966 | Menkart et al. | |
| 5,340,569 A * | 8/1994 | Elliott et al. | 424/63 |
| 5,499,825 A * | 3/1996 | Maeda et al. | 277/626 |
| 6,645,612 B2 * | 11/2003 | Pujari et al. | 428/325 |
| 6,951,583 B2 * | 10/2005 | Clere et al. | 106/287.3 |
| 2004/0185023 A1 | 9/2004 | Schnittger et al. | |
| 2007/0207101 A1 * | 9/2007 | Butts et al. | 424/63 |

FOREIGN PATENT DOCUMENTS

| | | |
|---|---|---|
| JP | 61-204111 | 9/1986 |
| JP | 06-100411 | 4/1994 |
| JP | 07-304647 | 11/1995 |
| JP | 10102083 A * | 4/1998 |
| JP | 2003327992 A2 | 11/2003 |
| JP | 2004-131413 | 4/2004 |
| JP | 2004315435 A2 | 11/2004 |
| JP | 2005-306872 | 11/2005 |
| JP | 20050276826 | 12/2005 |

* cited by examiner

*Primary Examiner* — Sreeni Padmanabhan
*Assistant Examiner* — Layla Soroush
(74) *Attorney, Agent, or Firm* — Dilworth & Barrese, LLP.

(57) ABSTRACT

A topical composition with a sustained softness feel to the skin, comprising an effective amount of boron nitride suspended in a dermatologically acceptable carrier vehicle, wherein the composition suitably adheres to the skin, leaving a coating layer comprising boron nitride particles. The present invention also relates to a method of massaging by applying the composition of the present invention on the body part to be massaged, and massaging the part coated with the composition of the invention.

2 Claims, No Drawings

COMPOSITIONS FOR TOPICAL APPLICATIONS COMPRISING BORON NITRIDE

CROSS-REFERENCE TO RELATED APPLICATIONS

This application claims the benefits of U.S. patent application Nos. 60/778539 filed Mar. 2, 2006 and 60/807528 filed Jul. 17, 2006,This application claims priority to and benefit from the foregoing, the disclosure of which is incorporated herein by reference.

FIELD OF THE INVENTION

The present invention relates to cosmetic compositions capable of exhibiting a beneficial effect on the skin.

BACKGROUND OF THE INVENTION

Various types of cosmetic compositions have been used in the prior art as massaging aids. Some compositions contain certain plant extracts as disclosed in Patent Publication No. JP 2004315435A2, with active ingredients including ginseng, ginkgo, hawthorn, tea extracts, and the like for effective massage without damaging the skin. Some compositions contain various essential oils as disclosed in Patent Publication No. JP 2003327992A2, with an essential oil consisting of hydrophilic polymer to reduce swelling in the body without carrying out a massage. Patent Publication No. JP 2005306872A2 discloses an oil-in-water-type emulsion topical composition having a water phase component, an oil component, polyol, monostearin acid polyethylene glycol, and glyceryl stearate/polyethylene glycol stearate as surface active agents.

In another prior art composition as disclosed in U.S. Pat. No. 3,250,680, Patent Application No. JP 61-204111, and Patent Application No. JP 06-100411, zeolite is added to promote blood circulation and to offer comfort, i.e., a warming sensation due to the heat of hydration of zeolite. U.S. Patent Publication No. 2004/0185023 discloses massaging compositions employing treated zeolite, e.g., encapsulated zeolite, as heat-generating agents.

Some topical compositions of the prior art often leave a greasy, sticky, or messy residue on the recipient of the massage from the active massaging component, e.g. essential oils, etc., which sometimes make it difficult for the masseur to do his/her job. Further, after a massaging session, the essential oils/gel residue from the topical composition can feel sticky and uncomfortable and can sometimes stain or soil the clothes of the wearer after he or she receives a massage.

Boron nitride is a ceramic material with unique properties including high lubricity, high thermal conductivity, low wear, and low thermal expansion. It has been used in a wide variety of applications, as an ingredient in industrial applications ranging from thermal spray coatings, thermal management greases, metallization boats, etc., to "high-tech" applications such as neutron detectors in homeland security systems. In cosmetic applications, boron nitride has been used in lipsticks, foundations, and face powders, where softness, lubricity, and opacity properties are desired. It has also been disclosed for topical applications, as in European Patent Publication No. EP 1055422, in a cosmetic or dermatological formulation including iron-titanium mixed oxide particles to improve the skin feel and protect the skin from the effects of sunlight.

There is still a need for improved topical compositions, e.g., massaging aid compositions. Applicants have found that boron nitride, with its unique lubricity and thermal conductivity properties, can be used in topical applications such as massaging that can easily be spread onto wide areas of the skin in massaging applications, leaving a pleasant cooling sensation on the skin of some of the wearers. In one embodiment, the massaging composition leaves a dry layer which may or may not be visible, comprising a very fine powder which facilitates the massaging of the skin by the masseur. In one embodiment, the topical composition leaves little, if any, residue on clothing of the recipient of a massaging session.

SUMMARY OF THE INVENTION

The invention, in one aspect, relates to a massaging method by topically applying to the part to be massaged a massaging effective amount of a composition comprising 0.1 to 99.9 wt. % boron nitride, wherein the composition, upon topical application onto the skin, leaves a layer comprising boron nitride particles.

In one aspect, the composition further comprises a dermatologically acceptable anhydrous carrier vehicle, selected from the group consisting of an organic solution, a gel, an aerosol, and an emulsifier and wherein the composition, upon topical application on the skin, leaves a residual layer having an L-value index ranging from 5 to about 100.

In another aspect, the invention relates to a topical composition comprising a dermatologically acceptable anhydrous carrier vehicle, having suspended therein, wherein the composition, upon topical application onto skin, suitably adheres to the skin, leaving a coating layer comprising boron nitride particles.

DESCRIPTION OF THE INVENTION

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases.

As used herein, in one embodiment the term "topical composition" means a "massaging composition," capable of facilitating the massage of the skin through rubbing actions by a human hand or a device to provide comfort to the skin/body being massaged. The term "massaging composition" also refers to a composition that facilitates or makes the job of a masseur easier than without the use of a massaging composition. The composition exhibits good spreadability, i.e., can be spread over or rubbed on the skin or body quickly over a wide area, and imparts a sustained soft feel to the skin.

As used herein, the term "masseur" denotes a device that functions to massage OR a person who massages a human body, facial skin, scalp, etc. to provide comfort, relaxation, and/or enjoyment for the person receiving the massage. A masseur does not have to be someone who is licensed or trained to massage others.

The term "suitable adherence to the skin" or "suitably adheres to the skin" means that the topical composition, after being applied to the skin, remains adhered to the skin long enough, under normal conditions of use, to have an efficacious effect. A layer of composition on the skin may be thought of as a stack of parallel thin layers, each layer being at least one molecule thick. With a composition that has suitable adherence to the skin, the composition's molecular layer closest to the skin (the bottom molecular layer) will temporarily bond physically and/or chemically to the skin on a molecular level, the composition's molecular layer above the bottom molecular layer will temporarily bond physically and/or chemically to that bottom molecular layer, and so on. The bonds between the skin and the bottom molecular layer and between the successive molecular layers cannot be permanent, or else it would be difficult to remove the composition from the skin.

The term "low residue" as used herein refers generally to the visible residue left on the applied areas of the skin or a surface during or immediately after application of the topical composition, and is used herein as a measure to help define the composition of the present invention. In this context, low residue measures the L-value, which is determined in accordance with the methodology described hereinafter.

All percentages and ratios used herein are by weight of the total composition and all measurements made are at 25° C., unless otherwise designated. Unless otherwise indicated, all percentages, ratios, and levels of ingredients referred to herein are based on the actual amount of the ingredient, and do not include solvents, fillers, or other materials which may be combined with the ingredient in commercially available products.

In one embodiment, the compositions intended for topical application on the skin, may be in the form of a lotion, cream, or fluid gel distributed as an aerosol spray, a pump-dispenser bottle, or as a roll-on; an ointment or thick cream distributed in a tube or a grille; a wand (stick); a bar; a mouse; a suspension; a dispersion; a water-disintegratable polymeric foam; an icy or hot application; or in a powder form. In one embodiment, the composition is applied or sprayed onto a sheet or other fabric/apparel for placing onto the skin area, which is to be subsequently massaged by a masseur.

The topical compositions may comprise ingredients generally used in products of the suitable form, e.g., cream, lotion, spray, etc., and well known to those skilled in the art, provided that they do not interfere with the boron nitride as the massaging active ingredient described herein. The ingredients useful herein may be categorized or described herein by their benefit or their postulated mode of action. However, it is to be understood that the active and other ingredients useful herein can, in some instances, provide more than one benefit or operate via more than one mode of action. Therefore, classifications herein are made for the sake of convenience and are not intended to limit an ingredient to the particularly stated application or applications listed.

Active Ingredient—Boron nitride: Boron nitrides, which can be in the topical composition of the invention, are commercially available from a number of sources, including, but not limited to, BN powder from GE Advanced Materials, Sintec Keramik, Kawasaki Chemicals, and St. Gobain Ceramics.

In one embodiment, the boron nitride is surface-treated ("coated") to further impart water repellent characteristics to the ingredient. Examples of surface coating materials for the boron nitride powder include, but are not limited to, avocado oil; isohexadecane; liquid paraffin; dimethylpolysiloxane (or dimethicone), a mixture of completely methylated, linear siloxane polymers which have been terminally blocked with trimethylsiloxy units; a silazane compound possessing perfluoroalkyl groups; a zirconate coupling agent; a zirconium aluminate coupling agent; an aluminate coupling agent; and mixtures thereof.

In one embodiment, the boron nitride powder particles have a primary average particle size of less than 250 µm. In a second embodiment, the primary average particle size is less than 50 µm. In a third embodiment, in the range of 10 to 30 µm. In a fourth embodiment, having a primary average particle size of less than 20 µm.

The total amount of boron nitride in the finished massaging formulation may be varied within wide parameters, but should be such a sufficient amount for the composition to leave a layer of boron nitride powder on the skin to effectively soften the skin to be massaged. As boron nitride has excellent thermal conductive properties compared to the active massaging ingredients of the prior art, in one embodiment, this amount is also sufficient for the person undergoing massage therapy to feel the heat and warmth transferred from the hands of the masseur as the person's body is being massaged. The amount is called a skin-softening effective amount for massaging or the massaging-effective amount.

Generally, in one embodiment, the massaging-effective amount is in the range of 0.1 to 99.9 wt. %, based on the total weight of the formulation. In another embodiment, the massaging-effective amount is 0.5 to about 90 wt. % BN. In a second embodiment, the amount ranges from 1 wt. % to 60 wt. %. In a third embodiment, from 5 wt. % to 40 wt. %. In a fourth embodiment, the amount ranges from 5 to 30 wt. %. In a fifth embodiment, this amount is between 2 to 15 wt. %. In a sixth embodiment, the amount of BN is 40-95 wt. %.

In one embodiment, the BN composition is applied in the pure BN powder form (i.e., consisting essentially of BN in an amount of 90 to 99.9 wt. %). The massaging powder composition comprises agglomerates of hBN platelets, with an agglomerate size distribution of from about 10 to about 250 µm. In another embodiment, the massaging powder composition consists essentially of hBN platelets having an aspect ratio of from about 10 to about 300. In a third embodiment, the massaging powder composition consists essentially of hBN particles having an oxygen content from 0.2 to 2.5 wt %. In a fourth embodiment, the massaging powder composition consists essentially of hBN particles having a graphitization index of less than 7.

In another embodiment, the topical composition is applied essentially as pure BN, but in the form of a stick or a wand with BN as the primary solid component. In one embodiment, the composition comprises 0 to 99.9 wt. % of hexagonal boron nitride (h-BN) and 0 to 99 wt. % of turbostratic boron nitride (t-BN). In another embodiment, a BN block is formed using the following process: a mixture of high oxygen t-BN and optional carbon additive is first cold pressed via a known method such as uniaxial pressing, filter pressing, or isostatic pressing, then heated to a temperature of 1500-2300° C. for 1 to 40 hrs., forming a block of sintered BN, having a density ranging from 0.20 to 1.50 g/cm$^3$.

For embodiments wherein the boron nitride component is used in a form other than pure BN powder, i.e., in a form with a carrier ingredient as a cream, a lotion, a liquid, etc., the topical composition may also comprise at least one adjuvant chosen from waxes, softeners, antioxidants, opacifiers, stabilizers, moisturizers, vitamins, fragrances, bactericides, preserving agents, polymers, fragrances, thickeners, propellants, or any other ingredient usually used for this type of topical application. A description of exemplary embodiments and ingredients follows.

Carrier Vehicle/Surfactant for the Topical Composition: In one embodiment, the topical composition for massaging applications is anhydrous. As used herein, "anhydrous" means a composition whose content is free of or having an added water level of less than 3%. In one embodiment, the content of added water is less than 1 wt. % relative to the total weight of the composition.

In one embodiment, the topical composition comprises a blend of liquid carrier and surfactant. Examples of surfactants include anionic, nonionic, and amphoteric surfactants, as long as they do not adversely interact with the ingredients used in the topical composition, nor in any way that may be irritating to the skin. Examples of nonionic surfactants include alkoxylated $C_{11}$-$C_{22}$ fatty alkyl hydrophobes. Examples of anionics and amphoterics include betaines. In one embodiment, nonionic surfactants are used to induce gelation, thus hardening the composition if applied in the form of a stick.

In one embodiment, the topical composition comprises at least one aqueous phase formulated, for example, in a form chosen from aqueous lotions, water-in-oil emulsions, oil-in-water emulsions, and multiple emulsions, e.g., oil-in-water-in-oil and water-in-oil-in-water triple emulsions (such emulsions are known and described, for example, by C. F. Fox in "Cosmetics and Toiletries", November 1986, Vol. 101, pages 101-112). In one embodiment, the at least one aqueous phase comprises water and generally other water-soluble or water-miscible solvents. The water-soluble or water-miscible solvents may be chosen from short-chain monoalcohols, for example, monoalcohols of $C_1$-$C_4$, such as ethanol and isopropanol; or from diols and polyols, for example, ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether, and sorbitol. In one embodiment, the carrier vehicle comprises propylene glycol and/or glycerol.

In one embodiment, the composition comprises at least one water-immiscible organic liquid phase. The at least one water-immiscible organic phase generally comprises at least one hydrophobic compound that renders the phase water-immiscible. The at least one water-immiscible organic phase is liquid (in the absence of a structuring agent) at room temperature (20-25° C.).

In one embodiment, the at least one water-immiscible organic liquid phase is chosen from an oil and a mixture of oils and comprises at least 80% of compounds with a vapor pressure not exceeding 4 kPa (30 mmHg) at 25° C. The at least one water-immiscible organic liquid phase, for example, comprises at least one emollient oil chosen from volatile and non-volatile, silicone-based, and hydrocarbon-based emollient oils. These emollient oils are, for example, described in U.S. Pat. Nos. 4,822,596 and 4,904,463.

As used herein, volatile silicones are defined, in a known manner, as being compounds that are volatile at room temperature. Mention may be made, for example, among these compounds, to cyclic and linear volatile silicones of the dimethylsiloxane type, whose chains comprise from 3 to 9 silicone-based residues. Cyclomethicones $D_4$, $D_5$ and $D_6$ may, for example, be used. As used herein, non-volatile silicones are defined, in a known manner, as being compounds with a low vapor pressure at room temperature, such as polyalkylsiloxanes; such as linear polyalkylsiloxanes, including linear polydimethylsiloxanes, or dimethicones; polyalkylarylsiloxanes, for example, polymethylphenylsiloxanes; and copolymers of polyether and siloxane, for example, dimethicone copolyols.

Among the non-volatile emollient oils that may be used, examples include hydrocarbon-based derivatives, mineral oils, fatty alcohols, esters of $C_3$-$C_{18}$ alcohols with $C_3$-$C_{18}$ acids, esters of benzoic acid with $C_{12}$-$C_{18}$ alcohols and mixtures thereof, $C_2$-$C_6$ polyols, for example, chosen from glycerol, propylene glycol or sorbitol, polyalkylene glycol polymers. In one embodiment, the emollient oil is present in an amount ranging from 1% to 50 wt. % of the composition. In a second embodiment, from 5% to 40 wt. %.

Other suitable liquid carriers include organic solvents. In one embodiment, the suitable organic solvents have a melting point of less than 10° C., which benefit both low-temperature storage stability and ease of manufacture. Examples include aliphatic alcohols (monohydric or polyhydric, preferably having 2 to 8 carbon atoms) and polyglycol ethers such as dipropylene glycol, glycerol propylene glycol, butylene glycol, ethanol, propanol, isopropanol, and industrial methylated spirits. Examples of organic solvents include aliphatic alcohols, such as ethanol and isopropanol. In one embodiment, the liquid carriers comprise at least one of a salicylate-based compound, such as glycol salicylate and methyl salicylate, acetone and menthol, for an icy cold sensation upon application.

Mixtures of carrier materials and/or surfactants are also usable. The total amount of carrier material employed is for some embodiments, from 30% to 99%, and for other embodiments, from 60% to 98%, expressed as a weight percentage of the total weight of the composition.

Structural/Filler Components: In one embodiment, the topical composition further includes at least one other agent that imparts structure to the composition or for gelling the at least one water-immiscible organic liquid phase of the composition, including organic structurants that are non-polymeric or polymeric. Examples of non-polymeric structurants include, but are not limited to, waxes and gellants, such as fatty acids or salts thereof, often containing from 12 to 30 carbons such as stearic acid or sodium stearate; and/or fatty alcohols (typically insoluble in water) often containing from 12 to 30 carbons; and elastomeric polyorganosiloxanes such as, those described in International Patent Application No. WO 97/44010.

The term "fatty" as used herein refers to a long chain aliphatic group, such as at least 8 or 12 linear carbons, which is frequently not branched (linear) and is typically saturated, but which can alternatively be branched and/or unsaturated. It is possible for the fatty acid to contain an hydroxyl group, as in 12-hydroxystearic acid, for example as part of a gellant combination, and to employ amino or ester derivatives thereof. Examples of suitable higher molecular weight alcohols include behenyl alcohol and sterols such as lanosterol.

The waxes may be chosen from animal, fossil, plant, mineral, and synthetic waxes. Mention may be made, for example, to beeswaxes, carnauba wax, candelilla wax, sugar cane wax, Japan wax, ozokerites, montan wax, microcrystalline waxes, paraffins, and silicone waxes and resins. The thickeners, which are, for example, non-ionic, may be chosen from modified and unmodified guar gums and celluloses, such as hydroxypropyl guar gum and cetylhydroxyethylcellulose .

In one embodiment, the topical composition further comprises stabilizers selected from particulate organic or inorganic materials, which are dispersible or dissolvable in the formulation. Examples include silica, mineral pigments, organic pigments, crosslinked polymers and copolymers of acrylic acid, cellulose ethers, and mixtures thereof. Examples of mineral pigments include, but are not limited to, calcium carbonate, titanium dioxide, clay, organophilic clay, talc, and gypsum.

In one embodiment, the stabilizer is in the form of a filler material selected from polyamide particles; polyethylene powders; microspheres based on acrylic copolymers, such as those made of ethylene glycol dimethacrylate/lauryl methacrylate copolymer; polymethyl methacrylate microspheres; ethylene-acrylate copolymer powders; expanded powders such as hollow microspheres and, for example, microspheres formed from a terpolymer of vinylidene chloride, of acrylonitrile and of methacrylate; powders of natural organic materials such as starch powders; silicone resin microbeads; amino acid powders such as lauroyllysine powder; and mixtures thereof.

In one embodiment, wherein the topical composition is in the form of a liquid stick, a cellulose ether, such as carboxymethyl cellulose and hydroxypropyl cellulose is added as a structurant in concentrations of up to 1.0%. In another embodiment, wherein structural components such as dibenzylidene sorbitol (DBS) are used, the composition may further comprise an amino acid salt in an amount effective to stabilize the DBS. In yet another embodiment, the composition comprises a solid triglyceride gellant as a structurant.

In one embodiment, the topical composition uses stearyl alcohol as a structural component in an amount of up to about 15% by weight.

In one embodiment, the topical composition is in the form of a water-disintegratable, polymeric foam that provides topical delivery of the massaging ingredients to the skin, while only slowly disintegrating and rinsing away with water during prolonged single-use or other similar application. In this embodiment, a surfactant paste containing the massaging ingredients is applied onto a disintegrated polymeric foam as disclosed in U.S. Patent Publication No. 20030180242A1, having a foam thickness of from about 0.2 mm to about 40 mm. The polymeric foam contains a structural component having a viscosity of less than about 15 cP in accordance with a Cold Water Insolubility Test and a viscosity of greater than about 10 cP in accordance with a Hot Water Solubility Test, selected from the group of consisting of polyvinyl alcohols, polyvinyl pyrrolidone, polyalkylene oxides, celluloses, cellulose derivatives, polysaccharides, polysaccharide derivatives, polycarboxylic acids, salts of polycarboxylic acids, polyamino acids, peptides, polyamides, polyacrylamides, polyesters, poly (vinyl methyl ether-co-maleic anhydride), alginates, alginate derivatives, pectins, polyethylene oxides, gelatins, carrageenans, chitosans, starches, starch derivatives, and combinations thereof.

Other Components: The composition of the invention also can comprise other components that may be chosen depending on the carrier and/or the type of formulation. The optional components are used in an amount that does not substantially, adversely impact the massaging effect.

In one embodiment, the topical composition further comprises a cosmetic or pharmacological component which functions as liquid carrier, as well as to provide soothing comfort to the body, e.g., a salicylate-based compound such as glycol salicylate and methyl salicylate, menthol, and mixtures thereof.

Propellant Component: In one embodiment wherein the topical composition is used as an aerosol application, the composition is used in a container/device which further contains at least one propellant for distributing the aerosol composition.

Examples of the propellants that are generally used with a massaging product of this type, include, but are not limited to, dimethyl ether (DME); and volatile hydrocarbons such as n-butane, propane, or isobutane, and mixtures thereof, optionally with at least one chlorohydrocarbon and/or fluorohydrocarbon including Freon™ and Dymel™. Carbon dioxide, nitrous oxide, nitrogen, or compressed air may also be used as the propellant. The topical composition and the at least one propellant may be in the same compartment or in different compartments in the aerosol container. In one embodiment, the concentration of propellant generally ranges from 5% to 95% by pressurized weight and, for example, from 50% to 85%, by weight relative to the total weight of the pressurized composition.

Preservative Compounds: In one embodiment, the topical composition may also include at least one preservative compound in combination with the boron nitride material. In one embodiment, the preservative compound is present in an amount of 0.5% and about 3% by weight of the formulation. Desirably, the preservative compound is effective against yeast, particularly *Candida albicans;* molds, particularly *Aspergillus niger;* and bacteria, particularly *S. aureus, E. coli,* and *E cloacae.* Examples include disodium ethylene diamine tetraacetic acid, methylparaben, and diazolidinyl urea. Disodium ethylene diamine tetraacetic acid also serves as a chelating agent to block the activity of bacterial ureases, lipases, proteases, and decarboxylases produced by *Klebsiella pneumoniae, Proteus mirabilis,* and *E. coli* bacteria, amongst others. Other preservative compounds known to those skilled in the art may also be used.

Bacteriostatic/Bactericidal Agents: In one embodiment, the topical composition comprises at least one additional bacteriostatic agent and/or bactericidal agent, such as 2,4,4'-trichloro-2'-hydroxydiphenyl ether (Triclosan), 2,4-dichloro-2'-hydroxydiphenyl ether, 3',4',5'-trichlorosalicylanilide, 1-(3', 4'-dichlorophenyl)-3-(4'-chlorophenyl)urea (Triclocarban) and 3,7,11 -trimethyldodeca-2,5,10-trienol (Famesol); quaternary ammonium salts, for example, cetyltrimethylammonium salts and cetylpyridinium salts; chlorhexidine salts; diglyceryl monocaprate, diglyceryl monolaurate and glyceryl monolaurate; and polyhexamethylene biguanide salts.

Fragrances: In one embodiment, the topical composition includes fragrances, which can be categorized into citrus, floral, spicy, lavender, woody, mossy, oriental, herbal, leather-tobacco and aldehydic groups. Typically, fragrance materials are supplied as concentrates, which generally contain up to about 3 percent fragrance by weight. Examples include natural products such as essential oils, flower oils, natural extracts from resins, gums, balsams, beans, mosses and other plants, and animal products such as ambergris and musk, as well as synthetic aromatic materials.

Characteristics of the Topical Composition of the Invention: The composition of the invention affords a non-sticky, non-waxy in-use, cooling effect, and lubricious characteristic upon application onto the skin, or a surface to be in contact with the skin of the person who is to receive a massage. When applied onto a surface such as the skin, a piece of cloth, or a surface, the composition forms a thin, low residue film on the applied surface. The applied film remains substantially as such over extended periods of time after application, thus allowing the skin to be effectively massaged and providing the needed therapeutic massaging feeling after the massage is over. When applied as a stick, a lotion, a cream, or in powder form directly onto the skin, the topical composition suitably adheres to the skin and provides a good glide feel to the skin, while still retaining good product stability.

In one embodiment, the topical composition is characterized as leaving a visible residue index of from 5 to about 100 L-value. In a second embodiment, the composition has a visible residue index of 10 to 80 L-value. In a third embodiment, the composition has an L-value of 30 to 50.

The term "visible residue index" as used herein refers generally to the extent to which the composition is visibly apparent as a thin topical film after application to the skin, and, more specifically, refers to visible residue values (expressed as an L-value on the L, a, b color scale). The L-value test is performed at 27° C., under atmospheric pressure, and at 15% relative humidity on a stick composition, having a product hardness of from about 500 gram-force to about 5,000 gram-force. In this test, a piece of black felt, approximately 10 cm×30 cm, is attached to a movable horizontal slide which is movably attached or fixed to a larger mechanical unit. An example of a suitable piece of black felt for use herein is Supreme Robe Velour, FN-6554, Color 404L, Style 31854, available from So-Fro Fabrics, Evendale, Ohio, U.S.A. An example of a suitable mechanical assembly for use herein is the Release and Adhesion Tester, Serial No. A-14934, manufactured by Testing Machines, Inc., Amityville, N.Y., U.S.A., or a Velmex Unislide Positioning System, Unislide assembly series (MB6000), available from Velmex, Inc., Bloomfield, N.Y., U.S.A. The massaging stick composition contained, within and partially extending out about 0.5 cm from a conventional package or container, is positioned perpendicular to and above the piece of felt, such that the product extends out of the package and faces the piece of felt. The surrounding package is positioned in place using a mechanical arm or other device suitable for applying the requisite movement to the product. The composition is then slowly moved toward and allowed to gently contact the attached piece of black felt. A 1,000 gram weight is placed on the product sample so that the product continuously contacts the piece of black felt during testing. The weighted sample is then moved repeatedly back and forth across the piece of felt at a fixed speed (about 3 cm/second), and with a fixed amount of applied pressure provided by the weighted product, until about 1.75 grams of the stick composition is evenly applied over a 5 cm×20 cm area of the piece of black felt. The piece of felt is then carefully removed from the apparatus. A calibrated Minolta CR-300 chromameter (available from Minolta Corp., Ramsey, N.J., U.S.A.) is then used to measure the L-value (on the L, a, b color scale) with an average L-value determined for multiple measurements.

Applications of the Topical Composition of the Invention: The topical composition can take any form which is typical of cosmetic products, for example: hot pour formulations, water-in-oil emulsions, oil-in-water emulsions, gels, sticks, sprays, anhydrous formulations, aerosol formulation, powder form, and the like.

In one embodiment, the massaging formulation is dispensed using a pump bottle for single-unit dosages, wherein the pump bottle is designed for sufficient individual dispensing, depending on the final application. In another embodiment, the massaging formulation is applied as single unit dosages in the form of a sheet, e.g., using an absorbent flexible substrate such as a non-woven cloth made from fibers or filaments. In one embodiment, the absorbent flexible substrate (e.g., in a sheet form) is soaked with an aqueous mixture of the topical composition. The resultant soaked sheet is pressed to remove any excess surfactant, and then dried, for single sheets having a sufficient amount of massaging formulation for single or individual massages.

In one embodiment, the composition of the invention may be used as a topical application to be applied directly to the skin, prior to the individual receiving a massage. In another embodiment, the composition (such as boron nitride powder or lotion) is applied onto a piece of cloth, then the cloth is used to rub/spread the topical composition onto the skin or body, prior to the individual receiving a massage.

Due to the lubricity of boron nitride as the active ingredient, the topical composition beneficially alters friction, between the masseur's hands and the skin being massaged, to enhance the tactile sensory perception of the person receiving the massage. The skin has a sustained soft feel to the touch, even after the skin is massaged extensively by a masseur. Additionally, due to the excellent thermal conductive property of the boron nitride material, the tactile sensory perception of the person receiving the massage is much further enhanced as having the masseur's hands in much closer contact with his/her muscles and skin than without the application of the topical composition of the invention. For the masseur, he/she can provide a much more effective massage with an "enhanced" feel for the skin of the person receiving the massage, with a skin that feels soft to the touch of the massager.

The invention is further illustrated by the following non-limiting examples. In application, the topical composition prepared in the examples below is rubbed against the skin or body parts to be receiving the massage, leaving a non-sticky thin residue/layer on the skin. After the skin is rubbed a few times, the white residue disappears leaving a nice smooth skin that is pleasant to the touch of the wearer. The skin portion that is in contact with the compositions of the invention also feels soft and smooth to the touch of the masseur, facilitating the massaging job.

EXAMPLES 1-5

Liquid Topical Composition

Liquid compositions are prepared having the ingredients and the amounts set out below. Each of these compositions is prepared by adding all of the ingredients to the cyclomethicone and mixing to form a homogeneous suspension.

| Ingredient in wt. % | Ex. 1 | Ex. 2 | Ex. 3 | Ex. 4 | Ex. 5 |
|---|---|---|---|---|---|
| Cyclomethicone (DC 344) | 74.5 | 73.5 | 66.90 | 60.50 | 59.85 |
| BN coated with polydimethylsiloxane | 21 | 22 | 28.6 | — | — |
| BN powder | — | — | — | 35 | 32.1 |
| Quaternium-18 hectorite | 3.5 | 3.5 | 3.5 | 3.5 | — |
| Propylene carbonate | 1 | 1 | 1 | 1 | — |
| Talc | — | — | — | — | 4.95 |
| Silica | — | — | — | — | 3.10 |

EXAMPLES 6-8

Aerosol Topical Composition

Aerosol compositions are prepared having the ingredients and the amounts set out below. Each of these compositions is prepared by adding all of the ingredients, except the propellant, to the cyclomethicone, and mixing to form a homogeneous suspension. The suspension is placed in an aerosol can and the propellant is added. In one embodiment, the propellant is a 1:2 blend of propellants 152A and A31.

| Ingredient in wt. % | Ex. 6 | Ex. 7 | Ex. 8 |
|---|---|---|---|
| Cyclomethicone (DC 344) | 24.6 | 26.13 | 23.13 |
| BN coated with polydimethylsiloxane | 13.18 | 11.65 | — |
| BN powder | — | — | 11.65 |
| Talc | 2.03 | 2.03 | 2.03 |
| Silica | 1.27 | 1.27 | 1.27 |
| Propellant | 58.92 | 58.92 | 58.92 |

EXAMPLES 9-12

Solid Stick Topical Composition

Solid stick compositions are prepared having the ingredients and the amounts set out below. Each of these compositions is prepared by mixing all of the ingredients, except the fragrance, with the cyclomethicone, heating the mixture to melt the gelling agents, and cooling the mixture to form a solid stick, with the fragrance being added during the cooling step and prior to solidification.

| Ingredient in wt. % | Ex. 9 | Ex. 10 | Ex. 11 | Ex. 12 |
|---|---|---|---|---|
| Cyclomethicone (DC 345) | 41.12 | 36.32 | 46.2 | 48.3 |
| BN coated with polydimethylsiloxane | 26.18 | 30.98 | — | — |
| BN powder | — | — | 29.2 | 27.9 |
| Stearyl alcohol | 15.53 | 15.53 | 15.53 | 15.53 |
| PPG-10 butanediol | 4.8 | 4.8 | — | — |
| C12-C15 alcohols benzoate | 3.84 | 3.84 | — | — |
| Hydrogenated castor oil | 2.84 | 2.84 | 3 | 3 |
| Myristyl myristate | 1.92 | 1.92 | 4 | — |
| PEG-8 distearate | 0.92 | 0.92 | — | 1 |
| Silica | — | — | 1.8 | 1.8 |
| Fragrance | 28.5 | 28.5 | 2.3 | 2.8 |

EXAMPLE 13

Solid Block/Stick Topical Composition Consisting Essentially of Boron Nitride:

A mixture comprising 29.4 wt. % h-BN powder with an oxygen content of 0.3 wt % (grade AC6004 from GE Advanced Materials), and 68.6 wt. % of t-BN with an oxygen content of 15 wt %, and 2 wt. % of carbon black (grade N991 from Cancarb) is homogenously blended together. The blend is pressed into a billet in a uniaxial press. The billet is then cut into a plurality of blocks. The blocks are then sintered for 10-30 hours at 1700-2300° C., forming low-density BN blocks with density ranging from 0.20 to 1.5 g/cm3, and with a fired $O_2$ concentration of <1.0 wt %.

EXAMPLES 14-16

Cream Topical Composition:

Cream compositions are prepared having the ingredients and the amounts set out below. Each of these compositions is prepared by adding all of the ingredients, except silica and fragrance, until uniform, heating to 50° C., then mixing under high shear agitation for twenty minutes. The mixture is passed through a Sonolator shear device to increase the viscosity. The fragrance is added last and is mixed until uniform.

| Ingredient in wt. % | Ex. 13 | Ex. 14 | Ex. 15 |
|---|---|---|---|
| Silicone latex (DC 2-9065) | 54.54 | 54.54 | 54.54 |
| Dimethicone (DC 225) | 10 | 10 | 9.31 |
| Cyclomethicone (DC 344) | 1.31 | 7.31 | — |
| BN coated with polydimethylsiloxane | 31.5 | 25.5 | — |
| BN powder | — | — | 33.50 |
| Trihydroxystearin | 0.4 | 0.4 | 0.4 |
| Hydrated silica (Sylox 2) | 1 | 1 | 1 |
| Fragrance | 1.25 | 1.25 | 1.25 |

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims, if they have structural elements that do not differ from the literal language of the claims, or if they include equivalent structural elements with insubstantial differences from the literal languages of the claims.

All citations referred herein are expressly incorporated herein by reference.

The invention claimed is:

1. A topical composition for applying onto the skin, a stick consisting essentially of boron nitride having a primary average particle size ranging from 10 to about 250 μm, wherein the composition, upon topical application onto skin, suitably adheres to the skin, leaving a coating layer consisting essentially of boron nitride particles, wherein said composition consists essentially of boron nitride in an amount of 90 to 99.9 wt. %.

2. A topical composition for applying onto the skin, comprising from 5 to 40 wt. % boron nitride, wherein the boron nitride has a graphitization index of less than 7, and wherein the composition is one of an aerosol, pump spray, liquid, roll-on, lotion, cream, gel, foam, or stick.

* * * * *